United States Patent [19]

Nakagawa et al.

[11] 4,283,570
[45] Aug. 11, 1981

[54] PROCESS FOR PREPARING RESORCINOL

[75] Inventors: Hiroaki Nakagawa, Iwakuni; Noriyuki Hirowatari, Ohtake; Takayuki Nakamura, Iwakuni, all of Japan

[73] Assignee: Mitsui Petrochemical Industries Ltd., Tokyo, Japan

[21] Appl. No.: 115,704

[22] Filed: Jan. 28, 1980

Related U.S. Application Data

[63] Continuation of Ser. No. 954,547, Oct. 25, 1978, abandoned, which is a continuation of Ser. No. 822,634, Aug. 8, 1977, abandoned.

[30] Foreign Application Priority Data

Aug. 18, 1976 [JP] Japan .................................. 51-97680

[51] Int. Cl.$^3$ .............................................. C07C 37/08
[52] U.S. Cl. ................................................... 568/768
[58] Field of Search ......................................... 568/768

[56] References Cited

U.S. PATENT DOCUMENTS

| | | | |
|---|---|---|---|
| 2,718,530 | 8/1955 | Conner | 568/768 |
| 2,735,871 | 2/1956 | Smith | 568/768 |
| 3,923,908 | 12/1975 | Suda et al. | 568/768 |

FOREIGN PATENT DOCUMENTS

| | | | |
|---|---|---|---|
| 35-13824 | 9/1960 | Japan | 568/768 |
| 748287 | 4/1956 | United Kingdom | 568/768 |
| 910735 | 11/1967 | United Kingdom | 568/768 |

*Primary Examiner*—Werren B. Lone
*Attorney, Agent, or Firm*—Sherman & Shalloway

[57] ABSTRACT

A process for preparing resorcinol in improved yields while avoiding the formation of reactive by-products which comprises
(1) a first step of pre-treating an oxidation product of m-diisopropylbenzene composed of m-diisopropylbenzene dihydroperoxide and by-product m-substituted carbinol hydroperoxide and/or dicarbinol with hydrogen peroxide in the presence of an acid catalyst in a heterogeneous system of an aqueous aromatic hydrocarbon solvent under conditions which do not substantially cause the acid cleavage, the pretreatment being performed while removing by-product water as an azeotrope with the aromatic hydrocarbon in the treating system, and
(2) a second step of acid-cleaving the pre-treated reaction product in the substantial absence of hydrogen peroxide.

15 Claims, No Drawings

PROCESS FOR PREPARING RESORCINOL

This is a continuation of application Ser. No. 954,547, filed Oct. 25, 1978, which in turn is a continuation of application Ser. No. 822,634, filed Aug. 8, 1977, both now abandoned.

This invention relates to an improved process for producing resorcinol in improved yields while avoiding the formation of reactive by-products and the troubles that will be caused by these by-products, such as the formation of other difficultly-removable by-products by reaction between the reactive by-products and resorcinol.

More specifically, the present invention relates to an improved process for producing dihydroxybenzenes, especially resorcinol, by the acid cleavage of oxidation products of diisopropylbenzenes, especially m-diisopropylbenzene, with hydrogen peroxide and an acid catalyst such as sulfuric acid, which comprises a first step of pretreating the starting oxidation product of diisopropylbenzene in the presence of hydrogen peroxide in a heterogeneous system of an aqueous aromatic hydrocarbon solvent under conditions which do not substantially cause acid cleavage, while removing the by-product water as an azeotrope with the aromatic hydrocarbon in the treating system, and a second step of acid-cleaving the pretreated product with an acid catalyst in the substantial absence of hydrogen peroxide.

It has been well known to produce dihydroxybenzenes by acid-cleaving of oxidation products of diisopropylbenzene with an acid catalyst, and improvements of such a method have also been suggested. For example, British Patent No. 910,735 (published on November 21, 1962) discloses that in the production of hydroquinone by acid-cleavage of an oxidation product of p-diisopropylbenzene, by-product p-substituted carbinol hydroperoxide is not converted to hydroquinone, but can be so converted by a one-step process of treatment with hydrogen peroxide in the presence of an acid catalyst in a homogeneous system of an inert solvent. The British Patent only describes the production of hydroquinone by one-step treatment in a homogeneous system, and does not at all disclose anything about the formation of resorcinol from by-product m-substituted carbinol hydroperoxide present as an oxidation product of m-diisopropylbenzene.

It was also suggested in Japanese Patent Publication No. 13824/60 (published on Sept. 21, 1960) to prepare phenols by treating by-product carbinols present in the oxidation products of alkyl benzenes with hydrogen peroxide in one step in the presence of an acid catalyst in a heterogeneous system. This Patent also fails to describe anything about the production of resorcinol, and all of the working examples in it relate to the production of phenols.

These prior suggestions commonly teach the conversion of by-product carbinols present in the oxidation products by one-step acid-cleavage with hydrogen peroxide in the presence of an acid catalyst, and do not at all refer to the conversion of by-product m-substituted carbinol hydroperoxides and/or dicarbinols present in the oxidation products of m-diisopropylbenzene to resorcinol.

The present inventors made investigations in an attempt to overcome the troubles which will be caused by the formation of by-products in the production of resorcinol from an oxidation product of m-diisopropylbenzene by acid cleavage.

The oxidation product of m-diisopropylbenzene to be acid-cleaved contains by-product m-substituted carbinol hydroperoxide such as 2-hydroxy-2-propyl-α,α-dimethylbenzyl hydroperoxide (formula 2) and by-product m-substituted dicarbinols such as di(2-hydroxy-2-propyl) benzene (formula 3)

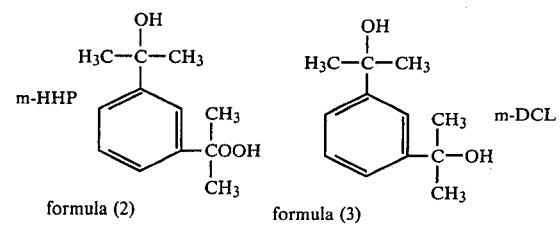

as well as m-diisopropylbenzene dihydroperoxide of formula (1)

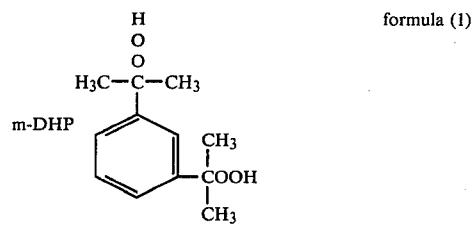

which can be converted to resorcinol.

The inventors found that when an oxidation product containing such by-products which cannot be converted to resorcinol by acid cleavage is subjected to acid cleavage in the presence of an acid catalyst, the yield of resorcinol is considerably reduced, and there are formed other by-products which are difficult to remove. The inventors tried to use the acid-cleavage techniques using hydrogen peroxide and an acid catalyst suggested by the British and Japanese patents cited above in an attempt to remove the troubles ascribable to the formation of by-products in the acid cleavage of an oxidation product of m-diisopropylbenzene consisting of m-substituted carbinol hydroperoxide and/or m-substituted dicarbinol and m-diisopropylbenzene dihydroperoxide. However, as shown in comparative examples given hereinbelow, they found that satisfactory yields of resorcinol could not be achieved because resorcinol tended to form a high-boiling substance by reaction with m-HHP or m-DCL.

The present inventors furthered their investigations in order to solve this new technical problem which arose in the acid cleavage of an oxidation product of m-diisopropylbenzene composed of m-diisopropylbenzene dihydroperoxide and by-product carbinol hydroperoxide and/or dicarbinol.

These investigations finally led to the discovery that this technical problem can be solved advantageously, and resorcinol can be produced in improved yields while avoiding the troubles ascribable to the formation of by-products which are difficult to separate from the final main product, by performing the acid cleavage of the oxidation product with hydrogen peroxide and an acid catalyst by a two-step reaction, wherein in a first step, the starting oxidation product is pre-treated with hydrogen peroxide in the presence of an acid catalyst in a heterogeneous system of an aqueous aromatic hydrocarbon solvent while removing the by-product water by azeotropic distillation under conditions which will not cause substantial acid cleavage, and in a second step, the pretreated reaction product is subjected to acid cleavage with an acid catalyst in the substantial absence of hydrogen peroxide.

When the one-step acid cleaving technique using hydrogen peroxide and an acid catalyst suggested in the above-cited British Patent is applied to the oxidation product used as a starting material in the present invention, the yield is at most about 55 mole % based on m-diisopropylbenzene dihydroperoxide, as shown in Comparative Example 3 below. When the technique suggested in the cited Japanese patent is applied to the oxidation product used as a starting material in this invention, the yield is as low as about 10 mole %, based on m-diisopropylbenzene dihydroperoxide as shown in Comparative Example 4. In contrast, according to the present invention, resorcinol can be produced in a very high yield of about 110 mole % or more and even about 115 mole % based on m-diisopropylbenzene dihydroperoxide without the formation of undesirable by-products.

It is an object of this invention to provide an improved process which can convert an oxidation product of m-diisopropylbenzene composed of by-product m-substituted carbinol hydroperoxide and/or dicarbinol, and m-diisopropylbenzene dihydroperoxide or these by-products separated from the oxidation product to resorcinol in high yields commercially advantageously and effectively while avoiding the formation of undesirable secondary by-products.

The above and other objects and advantages of this invention will become more apparent from the following description.

The method for producing the starting oxidation product of m-diisopropylbenzene used in this invention is well known. It can be produced by oxidizing m-diisopropylbenzene with a gas containing molecular oxygen, such as air. As needed, the reaction is carried out in the presence of an alkaline aqueous solution and a radical initiator such as dicumyl peroxide, benzoyl peroxide and azobisisobutyronitrile at a temperature of about 70° to about 130° C. at a pH of about 7 to about 11. The resulting oxidation product of m-diisopropylbenzene composed of m-diisopropylbenzene dihydroperoxide and by-product m-substituted carbinol hydroperoxide and/or dicarbinol may be directly used as a starting material in this invention. Or it may be used after removing the unreacted diisopropylbenzene from the oxidation product. Or the m-substituted by-products, which are separated from the oxidation product, may be used as the starting material. At this time, the separated by-products may be subjected to the first-step pre-treatment and then, the pre-treated by-products and the mother liquor left after the separation of the by-products may be subjected to the second step of acid cleavage. It is operationally advantageous to use the oxidation product directly after, if desired, removing the unreacted diisopropylbenzene from it.

In the first step of the process of this invention, the starting material described hereinabove is pre-treated with hydrogen peroxide in a heterogeneous system of an aqueous aromatic hydrocarbon solvent in the presence of an acid catalyst under conditions which will not substantially cause the acid cleavage of m-diisopropylbenzene dihydroperoxide while removing the water formed as by-product as azeotrope with the aromatic hydrocarbon in the treating system. The pre-treatment can induce the conversion of the m-substituted carbinol hydroperoxide and/or dicarbinol to m-diisopropylbenzene dihydroperoxide while avoiding the formation of secondary by-products.

The hydrogen peroxide used in the first step includes hydrogen peroxide itself, an aqueous solution of hydrogen peroxide, and substances which can generate hydrogen peroxide under the reaction conditions, such as sodium peroxide or calcium peroxide. The use of an aqueous solution of hydrogen peroxide is preferred. The amount of the hydrogen peroxide used is, for example, 2 to 20 equivalent times, preferably about 3 to 15 equivalent times of the total amount of the carbinol groups of m-substituted carbinol hydroperoxide and/or dicarbinol contained in the oxidation reaction product. If the amount is less than 2 equivalent times, the oxidation of the carbinols does not easily proceed, and even under severe conditions, only acid-cleavage takes place. On the other hand, amounts exceeding 20 equivalent times are undesirable because the efficiency of utilizing $H_2O_2$ decreases, and side-reactions increase. When the hydrogen peroxide is used in an amount exceeding 1 equivalent, the aqueous layer containing hydrogen peroxide after separating from the pre-treated product may be recycled for re-use either directly or after concentrating it and pre-treating it.

The first-step reaction is carried out in a heterogeneous system of an aqueous aromatic hydrocarbon solvent. Examples of the aromatic hydrocarbon solvent are benzene, toluene, xylene, ethylbenzene, cumene, cymene, and diisopropyl benzene. Of these, benzene, toluene, xylene and cumene are used preferably. These solvents may be used singly or as a mixture of two or more. The amount of the aromatic hydrocarbon solvent is about 0.2 to about 10 times, preferably about 0.5 to 2 times of the weight of the oxidation product of m-diisopropylbenzene or the by-products separated from the oxidation product. The aromatic hydrocarbon has the advantage that it does not form a homogeneous system in the presence of water, is stable to hydrogen peroxide, scarcely dissolves hydrogen peroxide, and is easy to separate from a ketone solvent in the second step.

Examples of the acid catalyst used in the first step include inorganic acids such as sulfuric acid, perchloric acid, hydrochloric acid and phosphoric acid, and organic acids such as chloroacetic acid and para-toluenesulfonic acid. The use of the inorganic acids, especially sulfuric acid, is preferred. The amount of the acid catalyst can be varied properly according, for example, to the pre-treating conditions and the type of the catalyst, and can be about 2.5 to 75% by weight, preferably about 10 to 40% by weight, based on the weight of the starting oxidation product or the starting by-products.

According to the process of this invention, the aqueous layer containing the unreacted hydrogen peroxide and the acid catalyst present in the pre-treated product in the first step may be recycled for re-use either directly or after being properly concentrated. The acid catalyst removed out of the reaction system is a small amount of the acid catalyst which is entrained by the aromatic hydrocarbon solvent layer. Usually, the amount of the acid catalyst so withdrawn is not more than about 0.3% by weight, usually about 0.1 to 0.3% by weight. In a reaction in a homogeneous system, the unreacted hydrogen peroxide and the acid catalyst cannot be recycled in such a way.

The reaction in a heterogeneous system in the first step can advantageously avoid the acid cleavage reaction and the formation of undesirable secondary by-products. Such an advantage cannot be easily obtained by reactions in a homogeneous system. Specific operating conditions such as the reaction temperature, the concentration of the acid catalyst, and the reaction time can be easily determined experimentally so that the acid cleavage rate ($A_1/A_0$), in which $A_0$ is the number of equivalents of the —OOH groups in starting material containing hydrogen peroxide fed into the reaction system, and $A_1$ is the number of equivalents of the —OOH groups in the reaction product, does not exceed about 2%. Generally, the reaction temperature is about 20° to 70° C., preferably about 30° to 60° C., more preferably about 40° to 55° C., and the reaction time is about 3 to 60 minutes, preferably about 5 to 15 minutes. The temperature and reaction time can be chosen properly according to the concentration of the acid catalyst used so that the acid cleavage rate may not exceed about 2%. When the reaction time is fixed, the acid catalyst may be used in a lower concentration as the reaction temperature is higher, and in a higher concentration as the reaction temperature is lower. In any case, acid cleavage tends more to occur if the temperature is higher, the concentration of the acid catalyst is higher, and the reaction time is longer. For example, when the temperature employed is about 40° C. while the reaction time is within the above range, the concentration of sulfuric acid used is about 15 to 25% by weight (about 1.7 to 2.9 moles/liter); about 8 to 20% by weight (about 0.92 to 2.3 moles/liter) when the temperature is about 50° C.; and about 5 to 15% by weight (about 0.58 to 1.7 moles/liter) when the temperature is about 60° C.

Preferred conditions in the first-step pre-treatment are: the reaction temperature, lower than 60° C.; the concentration of hydrogen peroxide in the aqueous solution of hydrogen peroxide in the pre-treatment system, 1 to 15 moles/liter (3 to 45% by weight), preferably 3 to 10 moles/liter (9 to 30% by weight); the concentration of the acid catalyst, 0.5 to 5 moles/liter, preferably 0.9 to 2.9 moles/liter.

The first-step reaction is carried out while removing the water formed as a by-product as an azeotrope with the pre-treating system. In the pre-treatment step, water is formed as a by-product from hydrogen peroxide, and the amount of water in the aqueous layer increases. This tends to decrease the concentration of hydrogen peroxide and the acid catalyst in the aqueous layer. By performing the reaction while removing the by-product water as an azeotrope, it is possible to maintain the rate of oxidation of the m-substituted carbinol hydroperoxide and/or dicarbinol at a suitable value. The pressure of the pre-treatment system may be a pressure at which the aromatic hydrocarbon solvent forms an azeotrope with water at the temperature employed. For example, the pressure may be about 50 to 200 mmHg. The pressure can be varied properly according, for example, to the reaction temperature, and the type of the aromatic hydrocarbon solvent. The pre-treating reaction may be performed either batchwise or continuously.

After the pre-treatment step described hereinabove, the pre-treated product is subjected to acid cleavage in the second step with an acid catalyst in the substantial absence of hydrogen peroxide.

The second step can be performed smoothly in the substantial absence of hydrogen peroxide by any known means of acid cleavage of the oxidation products of diisopropylbenzene. The pre-treated product, either directly or after distilling off a part or the whole of the aromatic hydrocarbon and if desired adding another solvent, is contacted with a solid catalyst. Usable acid catalysts include solid acids such as cation exchange resins, silica-alumina and silica-titania, as well as those exemplified for the acid catalyst used in the first step.

When the inorganic acid or organic acid illustrated for the first step is used, the reaction system is preferably uniform. For this purpose, a solvent which dissolves both the reaction product of the first step and the acid catalyst is used. Examples of such a solvent are acetone, methyl ethyl ketone, diethyl ketone, and methyl isobutyl ketone. The amount of the inorganic acid or organic acid is usually 0.1 to 15% by weight, preferably about 0.2 to 5% by weight, based on the reaction product of the first step. The acid cleavage reaction is carried out usually at a temperature of about 40° to 100° C., preferably about 70° to 90° C.

When a solid acid is used as the acid catalyst, the reaction system naturally becomes heterogeneous. In this case, too, it is preferred to use the aforesaid ketones as a reaction solvent. The amount of the solid acid is usually 2 to 100% by weight, preferably 20 to 80% by weight based on the pre-treated product obtained in the first step. The temperature used at this time is the same as that described above.

In the process of this invention, the use of the solid acid is preferred.

After the second-step reaction, resorcinol can be separated and recovered in a customary manner. For example, the solvent is distilled off from the acidcleaved product, and the residue is concentrated. Resorcinol can be isolated by known means such as distillation, crystallization or extraction.

The following examples illustrate the present invention in more detail.

EXAMPLE OF PREPARING THE STARTING MATERIAL

A mixture consisting of 100 parts by weight of meta-diisopropylbenzene and 10 parts by weight of a 3% by weight aqueous solution of sodium hydroxide was oxidized for 22 hours while blowing air with stirring at 100° C. The oxidation reaction was performed while intermittently feeding a 5% by weight aqueous solution of sodium hydroxide so as to maintain the pH of the reaction system at 8 to 10. After the oxidation, 187 parts by weight of toluene was added, and the separated alkaline aqueous layer was removed. The resulting toluene solution of the oxidation reaction product had the following composition.

| | |
|---|---|
| m-Diisopropylbenzene dihydroperoxide (m-DHP) | 19.6% by weight |
| By-product m-substituted carbinol hydroperoxide (m-HHP) | 7.7% by weight |
| By-product m-substituted dicarbinol (m-DCL) | 1.5% by weight |
| m-Diisopropylbenzene monohydroperoxide (m-MHP) | 6.4% by weight |
| Toluene | 58.4% by weight |
| Water | 2.5% by weight |
| Others | 3.9% by weight |

EXAMPLE 1

(1) A toluene solution of the oxidation reaction product of m-diisopropylbenzene prepared in the above example of preparing the starting material, and an aquous solution containing 18.2% by weight (concentration in the aqueous solution 6.05 moles/liter) of hydrogen hydroperoxide and 9.1% by weight (concentration in the aqueous solution 1.05 moles/liter) of sulfuric acid were continuously fed at a rate of 320.2 parts by weight per hour and 463.8 parts by weight per hour, respectively, into a tank-like reactor equipped with a stirrer and having a distillation column and a water-separating device provided at its upper part. The oxidation product was thus reacted with vigorous stirring at a reaction temperature of 50° C. and a reaction pressure of 130 to 140 mmHg with an average residence time of 10 minutes. At this time, the toluene phase in the distillate was entirely returned to the reaction system, and 82.7 parts by weight per hour of the water layer separated from the distillate was taken out from the reaction system. When the reaction mixture was continuously withdrawn, and subjected to phase separation, 328.8 parts by weight per hour of an oil layer was obtained. The concentration of m-DHP in this oily layer increased to 26.2% by weight. The oil layer was neutralized, washed with water, and concentrated and dehydrated under reduced pressure. The resulting product was diluted with the same amount of acetone to use it in the subsequent acid cleavage reaction.

The amount of the water layer obtained by separating the oil layer from the reaction mixture was 372.5 parts by weight per hour. The water layer contained 19.1% by weight of hydrogen peroxide and 11.3% by weight of sulfuric acid. It was recycled to the reaction system after adjusting the concentrations of hydrogen peroxide and sulfuric acid to the ones set forth hereinabove.

(2) A silica-alumina catalyst and the solution of the oxidation reaction product obtained by the procedure described in (1) above were continuously fed into a tank-type reactor equipped with a stirrer at a rate of 77 parts by weight per hour, and 346.1 parts by weight per hour. The resulting suspension was subjected to an acid cleavage reaction at a reaction temperature of 90° C. with an average residence time of 60 minutes while continuously withdrawing the reaction mixture. The silica-alumina was separated from the reaction mixture by filtration. Concentrating the filtrate afforded a viscous residue at a rate of 78.5 parts by weight per hour. The residue contained 43.8% by weight of resorcinol and 19.1% by weight of meta-isopropyl phenol. The yield of resorcinol was 113 mole% based on m-DHP contained in the starting oxidation reaction product.

Distillation of the viscous residue resulted in the separation of resorcinol and meta-isopropyl phenol.

COMPARATIVE EXAMPLE 1

(1) The same reaction as in Example 1, (1) was performed except that the entire distillate was refluxed. The reaction mixture withdrawn from the reactor was separated, and 326.0 parts by weight per hour of an oil layer and 458.0 parts by weight per hour of a water layer were obtained. The concentration of m-DHP in the oil layer was 23.8% by weight, and the concentrations of hydrogen peroxide and sulfuric acid in the water layer were 17.0% by weight (5.78 moles/liter) and 9.2% by weight (1.06 moles/liter), respectively. The water layer could not be entirely recycled in view of the balance of water in the reaction system. When the concentration of hydrogen peroxide was adjusted to 18.2% by weight by adding a 60% aqueous solution of hydrogen peroxide, it was necessary to withdraw 8.6 parts by weight per hour of the water layer out of the reaction system.

(2) The reaction mixture obtained by the procedure of (1) above was treated in the same way as in Example 1, (2) to perform an acid cleaving reaction. On distilling off acetone and toluene, 78.2 parts by weight per hour of a residue was obtained. The residue contained 38.6% by weight of resorcinol and 18.1% by weight of meta-isopropyl phenol. The yield of resorcinol was 97 mole% based on m-DHP contained in the starting oxidation reaction product obtained in the foregoing example of preparing the starting material.

The result shows that if the by-product water was not removed as an azeotrope, m-HHP and m-DCL in the starting material could not be sufficiently oxidized with hydrogen peroxide by using the same amounts of hydrogen peroxide and sulfuric acid as in Example 1, and consequently the yield of resorcinol decreased by 16 mole% from that in Example 1.

COMPARATIVE EXAMPLE 2

(1) The same procedure as in Comparative Example 1, (1) above was repeated except that an aqueous solution containing 21.3% by weight (7.08 moles/liter) of hydrogen peroxide and 11.1% by weight (1.28 moles/liter) of sulfuric acid was continuously fed at a rate of 508.6 parts by weight per hour. When the reaction mixture was separated, an oil layer and an aqueous layer were obtained at a rate of 328.8 parts by weight per hour, and 500.0 parts by weight per hour, respectively. The oil layer contained m-DHP in a concentration of 26.2% by weight, and the water layer contained hydrogen peroxide in a concentration of 19.1% by weight.

The water layer could not be entirely recycled in view of the balance of water in the reaction system. When the concentration of hydrogen peroxide was adjusted to 21.3% by weight by adding a 60% aqueous solution of hydrogen peroxide, it was necessary to withdraw 23.1 parts by weight per hour of the water layer out of the reaction system.

When the oil layer obtained by this reaction was treated in the same way as in Example 1, (2), resorcinol was obtained in a yield of 96 mole%.

COMPARATIVE EXAMPLE 3

A toluene solution of the oxidation reaction product prepared in the above example of preparing the starting material, a 60% by weight aqueous solution of hydrogen peroxide, and an acetone solution containing 0.8% by weight of sulfuric acid were continuously fed at a rate of 320.2, 13.3, and 333.5 parts by weight per hour, respectively, and a one-step reaction in a homogeneous system was performed at a reaction temperature of 70° C. with an average residence time of 30 minutes to simultaneously perform oxidation with hydrogen peroxide and acid cleavage of dihydroperoxide. The homogeneous reaction mixture withdraw from the reactor was neutralized, and the solvents were distilled off under reduced pressure. A viscous residue was obtained at a rate of 81.3 parts by weight per hour. The residue contained 20.7% by weight of resorcinol and 16.8% by weight of meta-isopropyl phenol, but did not contain m-DHP, m-MHP and m-DCL. The yield of resorcinol in this case was 55 mole% based on the dihydroperoxide contained in the starting oxidation reaction product obtained in the example of preparing the starting material.

COMPARATIVE EXAMPLE 4

To 100 g of a toluene solution containing an oxidation reaction product of the compositions shown in Table 1 was added 100 g of an aqueous solution containing 1.5% by weight (0.50 mole/liter) of hydrogen peroxide and 10% by weight (1.15 moles/liter) of sulfuric acid. The oxidation product was reacted at 60° C. The heterogeneous reaction solution was analyzed at the end of 10 minutes, 1 hour, and 2 hours, respectively, after the initiation of the reaction. The results are shown in Table 1.

After a reaction time of 10 minutes, no change was seen in the concentration of hydrogen peroxide, and no substantial change was seen either in the concentration of total HPO (hydroxyperoxide). It can be understood therefore that acid cleavage took place, but no oxidation by hydrogen peroxide occurred.

When two hours passed after the initiation of the reaction, 0.23 g of resorcinol was formed, and this corresponded to a yield of 9 mole% based on m-DHP.

TABLE 1

| Components | (% by weight) | | | |
|---|---|---|---|---|
| | Raw material | 10 minutes | 1 hour | 2 hours |
| Oil layer | | | | |
| m-DHP | 14.82 | 14.82 | 13.60 | 9.56 |
| m-HHP | 4.60 | 4.60 | 1.41 | 0.71 |
| m-DCL | 0.30 | 0.30 | 0.30 | 0.30 |
| m-MHP | 1.88 | 1.88 | 2.64 | 2.71 |
| m-Acetyl isopropyl-benzene hydroperoxide | 1.02 | 1.02 | 1.54 | 1.38 |
| m-Hydroxy-isopropyl-benzene hydroperoxide | 0 | 0 | 1.38 | 2.18 |
| Total hydroperoxide (calculated as m-MHP) | 32.55 | 33.24 | 30.38 | 23.64 |
| Water layer | | | | |
| $H_2O_2$ | 1.51 | 1.51 | 1.51 | 1.51 |

What we claim is:

1. A process for preparing resorcinol from an oxidation product of diisopropylbenzene which comprises
    (1) a first step of pre-treating an oxidation product of m-diisopropylbenzene composed of m-diisopropylbenzene dihydroperoxide and by-product m-substituted carbinol hydroperoxide and/or dicarbinol with hydrogen peroxide in the presence of sulfuric acid as an acid catalyst in a heterogeneous system of an aqueous aromatic hydrocarbon solvent at a temperature of from about 30° C. to 60° C., for a reaction time of from about 3 minutes to about 60 minutes, the pre-treatment being performed while removing by-product water as an azeotrope with the aromatic hydrocarbon in the treating system, while maintaining the concentrations of the hydrogen peroxide and the acid catalyst in the aqueous solution of the treating system at 1 to 15 moles/liter, and 0.5 to 5 moles/liter, respectively, separating the aromatic hydrocarbon solvent layer containing the pre-treated reaction product from the aqueous layer containing the hydrogen peroxide of the first step pre-treatment; and
    (2) a second step of acid-cleaving the pre-treated reaction product recovered in the aromatic hydrocarbon solvent layer, in the substantial absence of hydrogen peroxide at a temperature of about 40° to 100° C., the second step being performed in the presence of an acid-cleavage catalyst selected from the group consisting of sulfuric acid and silica-alumina, the amount of sulfuric acid being 0.1 to 15% by weight, based on the pre-treated reaction product and the amount of silica-alumina being 2 to 100% by weight based on the pre-treated reaction product and recovering the resorcinol.

2. The process of claim 1 wherein the concentration of the sulfuric acid catalyst in the first step is 0.9 to 2.9 moles/liter.

3. The process of claim 1 wherein the total amount of hydrogen peroxide used in the pre-treatment is 2 to 20 equivalents based on the total amount of the carbinol groups in the by-products.

4. The process of claim 1 wherein the aromatic hydrocarbon solvent is selected from the group consisting of benzene, toluene, cumene and xylene.

5. The process according to claim 1 wherein the total amount of hydrogen peroxide used in the pre-treatment is 3 to 15 equivalents based on the total amount of the carbinol groups in the by-products and wherein the reaction time of the pre-treatment is from about 5 to 15 minutes.

6. The process according to claim 1 wherein the aqueous layer of the heterogeneous system containing unreacted hydrogen peroxide and acid catalyst is recycled to the step (1) pre-treatment.

7. The process according to claim 1 wherein the reaction temperature, concentration of acid catalyst and reaction time of the step (1) pre-treatment are such that the acid cleavage rate ($A_1/A_0$), in which $A_0$ is the number of equivalents of the —OOH groups in the oxidation product feed and $A_1$ is the number of equivalents of the —OOH groups in the reaction product, does not exceed about 2 percent.

8. A process for preparing resorcinol from m-diisopropyl benzene dihydroperoxide which comprises
    (1) pre-treating at least one by-product obtained from the oxidation of m-diisopropylbenzene to m-diisopropylbenzene dihydroperoxide, said by-product selected from the group consisting of m-substituted carbinol hydroperoxide and dicarbinol, with hydrogen peroxide in the presence of an acid catalyst selected from the group consisting of sulfuric acid, perchloric acid, hydrochloric acid, phosphoric acid, chloroacetic acid and paratoluene sulfonic acid in a heterogeneous system of an aqueous aromatic hydrocarbon solvent at a temperature of about 30° C. to 60° C., for a reaction time of about 3 minutes to about 60 minutes, while removing by-product water as an azeotrope with the aromatic hydrocarbon in the treating system, while maintaining the concentrations of the hydrogen peroxide and acid catalyst in the aqueous solution of the heating system, at 1 to 15 moles/liter, and 0.5 to 5 moles/liter, respectively, separating the aromatic hydrocarbon solvent layer containing the pre-treated reaction product from the aqueous layer containing the hydrogen peroxide of the first step pre-treatment; and
    (2) a second step of acid-cleaving the pre-treated reaction product recovered in the aromatic hydrocarbon solvent layer, in the substantial absence of hydrogen peroxide, at a temperature of about 40° C. to 100° C., the second step being performed in the presence of acid-cleaving catalyst selected from the group consisting of sulfuric acid and silica-alumina, the amount of sulfuric acid being 0.1 to 15% by weight, based on the the pre-treated reaction product and the amount of silica-alumina being 2 to 100% by weight, based on the pre-treated reaction product and recovering the resorcinol.

9. The process of claim 8 wherein the step (1) pre-treatment is carried out on the by-product m-substituted carbinol hydroperoxide or dicarbinol or both in the presence of the m-diisopropylbenzene dihydroperoxide oxidation product of m-diisopropylbenzene.

10. The process of claim 8 wherein the step (1) pre-treatment is carried out on the by-product, m-substituted carbinol hydroperoxide or dicarbinol or both which has been separated from the m-diisopropylbenzene dihydroperoxide obtained from the oxidation of m-diisopropylbenzene and wherein the step (2) acid-cleaving is performed after recombining the m-diisopropylbenzene dihydroperoxide oxidation product with the pre-treated by-product.

11. The process of claim 8 wherein sulfuric acid is used as the acid catalyst in the step (1) pre-treatment.

12. The process of claim 8 wherein the total amount of hydrogen peroxide used in the pre-treatment is 2 to 20 equivalents based on the total amount of the carbinol groups in the by-products.

13. The process according to claim 8 wherein the total amount of hydrogen peroxide used in the pre-treatment is 3 to 15 equivalents based on the total amount of the carbinol groups in the by-products and wherein the reaction time of the pre-treatment is from about 5 to about 15 minutes.

14. The process according to claim 8 wherein the aqueous layer of the heterogeneous system containing unreacted hydrogen peroxide and acid catalyst is recycled to the step (1) pre-treatment.

15. The process according to claim 8 wherein the reaction temperature, concentration of acid catalyst and reaction time of the step (1) pre-treatment are such that the acid cleavage rate ($A_1/A_0$), in which $A_0$ is the number of equivalents of the —OOH groups in the oxidation product feed and $A_1$ is the number of equivalents of the —OOH groups in the reaction product, does not exceed about 2 percent.

* * * * *